(12) United States Patent
Campbell et al.

(10) Patent No.: US 7,943,796 B2
(45) Date of Patent: May 17, 2011

(54) LUBRICATING OIL ADDITIVE AND LUBRICATING OIL COMPOSITION CONTAINING SAME

(75) Inventors: Curtis B. Campbell, Hercules, CA (US); Charles Michael Cisson, Walnut Creek, CA (US)

(73) Assignee: Chevron Oronise Company LLC, San Ramon, CA (US)

( * ) Notice: Subject to any disclaimer, the term of this patent is extended or adjusted under 35 U.S.C. 154(b) by 410 days.

(21) Appl. No.: 12/221,171

(22) Filed: Jul. 31, 2008

(65) Prior Publication Data

US 2010/0029527 A1  Feb. 4, 2010

(51) Int. Cl.
C07C 51/15 (2006.01)
C07C 321/28 (2006.01)
C07C 65/03 (2006.01)
C07C 39/235 (2006.01)

(52) U.S. Cl. ........ 562/424; 562/431; 562/475; 562/476; 508/586

(58) Field of Classification Search .................. None
See application file for complete search history.

(56) References Cited

U.S. PATENT DOCUMENTS

| | | | |
|---|---|---|---|
| 2,360,302 A | 10/1944 | Etzler et al. | |
| 2,592,428 A | 4/1952 | Kemp et al. | |
| 2,680,096 A | 6/1954 | Walker et al.. | |
| 2,814,655 A | 11/1957 | Langlois et al. | |
| 3,178,368 A | 4/1965 | Hauneman | |
| 3,368,972 A | 2/1968 | Otto | |
| 3,388,063 A | 6/1968 | Allphin, Jr. | |
| 3,429,812 A | 2/1969 | Kivelevich | |
| 3,649,229 A | 3/1972 | Otto | |
| 3,801,507 A | 4/1974 | Henrickson et al. | |
| 3,887,634 A | 6/1975 | Hughes | |
| 4,157,309 A | 6/1979 | Wilgus et al. | |
| 4,435,601 A | 3/1984 | Formanek et al. | |
| 5,281,346 A | 1/1994 | Adams et al. | |
| 5,370,805 A | 12/1994 | Smrcka et al. | |
| 5,458,793 A | 10/1995 | Adams et al. | |
| 5,510,043 A | 4/1996 | Inoue | |
| 5,759,966 A | 6/1998 | Campbell | |
| 6,340,659 B1 | 1/2002 | Kucsis et al. | |
| 6,372,696 B1 | 4/2002 | Tipton | |
| 6,551,967 B2 * | 4/2003 | King et al. | 508/391 |
| 2005/0288194 A1 | 12/2005 | Small et al. | |
| 2007/0049508 A1 | 3/2007 | Stonebraker et al. | |
| 2008/0269351 A1* | 10/2008 | Campbell et al. | 514/731 |

FOREIGN PATENT DOCUMENTS

| | | |
|---|---|---|
| EP | 1 760 135 | 3/2007 |
| GB | 734605 | 9/1955 |
| GB | 734622 | 9/1955 |

OTHER PUBLICATIONS

Ambient Aquatic Life Water Quality Criteria for Nonylphenol-Draft, United States Environmental Protection Agency, Office of Water 4304T, EPA 822-R-03-029, Dec. 2003, pp. 1-71, www.cpa.gov/waterscience/criteria/nonphenol.

Watanabe et al., Tissue-specific estrogenic and non-estrogenic effects of a xenoestrogen, nonlyphenol, Journal of Molecular Endocrinology, (2004), pp. 243-252, vol. 33, 2004 Society of Endocrinology, Printed in Great Britain, 0952-5041/04/033-243, www.indocrinology.org.

Tabira et al., Structural requirements of para-alkylphenols to bind to estrogen receptor, Eur. J. Biochem (1999) pp. 240-245, vol. 262, FEBS 1999.

Routledge et al., Structural Features of Alkylphenolic Chemicals Associated with Estrogenic Activity, The Journal of Biological Chemistry, 1997, pp. 3280-3288, vol. 272, No. 6, Issue of Feb. 7, 1997 by the American Society for Biochemistry and Molecular Biology, Inc., www-jbc.standford.edu/jbc/.

Alkylphenols & Ethoxylates Research Council, Alkylphenols and Alkylphenol Ethoxylates, an Overview of Safety Issues, Jan. 1999, APE Research Council: White Paper, pp. 1-9, www.aperc.org/docs/whitepaper-overview.html.

George et al., Final Report, Assessment of Pubertal Development and Thyroid Function in Juvenile Female CD® (Sprague-Dawley) Rats After Exposure to Selected Chemicals Administered by Gavage on Postnatal Days 22 to 42/43, RTI Identification Number: 65U-08055.001.015.002, RN Protocol No. RTI-830, pp. 1-52, www.epa.gov/scipoly/oscpendo/assayvalidation/status.html, Mar. 28, 2005.

* cited by examiner

Primary Examiner — Brian J Davis

(57) ABSTRACT

An overbased salt of an oligomerized alkylhydroxyaromatic compound is disclosed, wherein the alkyl group of the alkylhydroxyaromatic compound is derived from an olefin mixture comprising propylene oligomers having an initial boiling point of at least about 195° C. and a final boiling point of no more than about 325° C. as measured by ASTM D86. Also disclosed is a lubricating oil composition containing at least (a) a major amount of an oil of lubricating viscosity and (b) the overbased salt of the oligomerized alkylhydroxyaromatic compound.

45 Claims, No Drawings

LUBRICATING OIL ADDITIVE AND LUBRICATING OIL COMPOSITION CONTAINING SAME

BACKGROUND OF THE INVENTION

1. Technical Field

The present invention generally relates to a lubricating oil additive and lubricating oil composition containing same.

2. Description of the Related Art

There is increasing evidence that certain synthetic and natural chemicals may act as agonists or antagonists to estrogens or androgens and may interfere in multiple ways with the action of thyroid hormones. These chemicals can be called endocrine disruptors. For example, endocrine disruptors can (1) mimic or block chemicals naturally found in the body thereby altering the body's ability to produce hormones, (2) interfere with the way hormones travel through the body, and (3) alter the concentration of hormones reaching hormone receptors.

Endocrine disruptors and natural estrogens share a common mechanism of action. In normal cases, estrogenic activity is produced by binding natural estrogen to an estrogen receptor (ER) within the nucleus of the cell, followed by transcriptional activation of these occupied ERs. When endocrine disruptors are present, normal estrogenic activity is supplanted when endocrine disruptors bind an ER, causing transcriptional activation of the ER even though no natural estrogen is present. Similarly, antiestrogenic activity is produced by endocrine disruptors which bind to ERs, but which do not subsequently activate the occupied ER as well as natural estrogen. Finally, selective estrogen receptor modulators (SERMs) bind to ERs, but subsequently activate cellular responses that differ from those activated by the natural estrogens. In general, all but a very small number of molecules that bind to ERs produce some activation of the receptors, as either estrogens or as SERMs.

Alkylphenols and products produced from them have come under increased scrutiny due to their association as potential endocrine disruptive chemicals. This is due to the weak estrogenic activity of base alkylphenol as well as degradation intermediates of the alkylphenol products. Alkylphenols are commercially used in, for example, herbicides, gasoline additives, dyestuffs, polymer additives, surfactants, lubricating oil additives and antioxidants. In recent years, alkylphenol alkoxylates, such as ethoxylated nonylphenol, have been criticized for having poor biodegradability, high aquatic toxicity of the by-products of the biodegradation of the phenol portion. Thus, there is an increasing concern that these chemicals may act as endocrine disrupters. Some studies have shown there to be a link between alkylphenols and declining sperm count in human males and there is evidence that alkylphenols may harmfully disrupt the activity of human estrogen and androgen receptors. Specifically, Routledge et al., "Structural features of alkylphenolic chemicals associated with estrogenic activity", J Biol. Chem., 1997 Feb. 7; 272(6): 3280-8, compared different alkylphenols estrogenic activity in an estrogen-inducible strain of yeast comparing the assays with 17β-estradiol. The results indicated that optimal estrogenic activity requires a single branched alkyl group composed of between 6 and 8 carbon atoms located at the para position on an otherwise unhindered phenol ring with 4-tert-octylphenol (8 carbons also named 4-(1,1,3,3-Tetramethyl-butyl)-phenol)) having the highest activity. Routledge et al. tested various alkylphenols in the assay and indicated that alkyl chain length, degree of branching, location on the ring, and degree of isomeric heterogeneity affect the binding efficiency but was not able to draw a structure activity conclusion. For example, Routledge et al. stated that the p-nonylphenol as determined by high resolution gas chromatographic analysis identified 22 para-isomers speculating that all isomers would not have similar activity without elucidating the active species. Interestingly, Tabria et al., "Structural requirements of para-alkylphenols to bind to estrogen receptor", Eur. J. Biochem. 262, 240-245 (1999) found that when using human estrogen receptors, the receptor binding of alkylphenols was maximized when the number of alkyl carbons was nine carbon atoms. Tabria et al. noted that branched chain nonylphenol, mixture of isomers (commercially available and which did not contain any n-nonylphenol) was almost as active as n-nonylphenol.

Nonylphenol ethoxylate and octylphenol ethoxylate are widely used as nonionic surfactants. Concern over the environmental and health impact of these alkoxylated alkylphenols has led to governmental restriction on the use of these surfactants in Europe, as well as voluntary industrial restrictions in the United States. Many industries have attempted to replace these preferred alkoxylated alkylphenol surfactants with alkoxylated linear and branched alkyl primary and secondary alcohols, but have encountered problems with odor, performance, formulating, and increased costs. Although the predominate focus has been on the alkylphenol ethoxylates and the potential problems associated with these compounds (primarily with the degradation by-products), there remains a need to review other components to select combinations that have similar or improved performance benefits with reduced negative impacts.

Nonylphenol and dodecylphenol can be produced by the following steps: propylene oligomerization and separation of propylene trimer and tetramer, and phenol alkylation with propylene trimer and separation of nonylphenol, or phenol alkylation with propylene tetramer and separation of dodecylphenol. Tetrapropenyl phenol prepared from propylene tetramer has been widely used in the lubricant additive industry. A tetramer is a highly branched chain of 10 to 15 carbons with a high degree of methyl branching that imparts oil solubility and compatibility with other oil soluble lubricant additive components. A tetramer is also a cost effective olefin to manufacture. Dodecylphenol derived from propylene tetramer is primarily used as an intermediate in the production of additives for lubricating oils, commonly sulfurized alkyl phenate detergents. To a lesser degree, these branched phenate detergents have employed some degree of linear olefin.

U.S. Patent Application Publication No. 20070049508 ("the '508 application") discloses a lubricating oil composition containing (a) an oil of lubricating viscosity, and (b) a detergent containing an unsulfurized alkali or alkaline earth metal salt of a reaction product of (i) an olefin having at least 10 carbon atoms, wherein greater than 80 mole % of the olefin is a linear $C_{20}$ to $C_{30}$ n-alpha olefin, wherein less than 10 mole % of the olefin is a linear olefin of less than 20 carbon atoms, and wherein less than 5 mole % of the olefin is branched chain olefin of 18 carbons or less, and (2) a hydroxyaromatic compound. Comparative Example C in the '508 application discloses a branched pentadecylphenol calcium salt prepared by alkylating a phenol with a branched chain $C_{14}$ to $C_{18}$ olefin derived primarily from propylene pentamer. However, the '508 application discloses that the branched pentadecylphenol calcium salt of Comparative Example C was ineffective in preventing endocrine disruption effects.

U.S. Pat. No. 5,510,043 ("the '043 patent") discloses a lubricating oil additive containing (a) an alkaline earth metal salt of a sulfurized monoalkylcatechol derivative and (b) a sulfurized monoalkylcatechol. The '043 patent further discloses that the sulfurized monoalkylcatechol can be obtained by sulfurizing an alkylation product of a catechol produced by reacting a catechol with an olefin such as a propylene pentamer in the presence of a catalyst. There is no disclosure in the '043 patent of endocrine disruption effects.

It is desirable to develop improved lubricating oil additives for use in lubricating oil compositions that do not exhibit endocrine disruption effects.

SUMMARY OF THE INVENTION

In accordance with one embodiment of the present invention, there is provided an overbased salt of an oligomerized alkylhydroxyaromatic compound, wherein the alkyl group of the alkylhydroxyaromatic compound is derived from an olefin mixture comprising propylene oligomers having an initial boiling point of at least about 195° C. and a final boiling point of no more than about 325° C. as measured by ASTM D86.

In accordance with a second embodiment of the present invention, a process for preparing an overbased salt of an oligomerized alkylhydroxyaromatic compound, the process comprising the steps of:

(a) alkylating a hydroxyaromatic compound with an olefin mixture comprising propylene oligomers having an initial boiling point of at least about 195° C. and a final boiling point of no more than about 325° C. as measured by ASTM D86, to provide an alkylhydroxyaromatic compound;

(b) neutralizing the alkylhydroxyaromatic compound of step (a) to provide a salt of the alkylhydroxyaromatic compound;

(c) oligomerizing the salt of the alkylhydroxyaromatic compound of step (b) to provide a salt of an oligomerized alkylhydroxyaromatic compound; and (d) overbasing the salt of the oligomerized alkylhydroxyaromatic compound of step (c) to provide the overbased salt of the oligomerized alkylhydroxyaromatic compound.

In accordance with a third embodiment of the present invention, a lubricating oil composition is provided which comprises (a) a major amount of an oil of lubricating viscosity; and (b) an overbased salt of an oligomerized alkylhydroxyaromatic compound, wherein the alkyl group of the alkylhydroxyaromatic compound is derived from an olefin mixture comprising propylene oligomers having an initial boiling point of at least about 195° C. and a final boiling point of no more than about 325° C. as measured by ASTM D86.

In accordance with a fourth embodiment of the present invention, there is provided a method for reducing the endocrine disrupting properties of a lubricating oil composition on exposure to mammals, the method comprising adding an overbased salt of an oligomerized alkylhydroxyaromatic compound, wherein the alkyl group of the alkylhydroxyaromatic compound is derived from an olefin mixture comprising propylene oligomers having an initial boiling point of at least about 195° C. and a final boiling point of no more than about 325° C. as measured by ASTM D86, to a lubricating oil composition comprising a major amount of an oil of lubricating viscosity.

In accordance with a fifth embodiment of the present invention, the use of an overbased salt of an oligomerized alkylhydroxyaromatic compound, wherein the alkyl group of the alkylhydroxyaromatic compound is derived from an olefin mixture comprising propylene oligomers having an initial boiling point of at least about 195° C. and a final boiling point of no more than about 325° C. as measured by ASTM D86, as an additive in a lubricating oil composition comprising a major amount of an oil of lubricating viscosity for the purpose of reducing the endocrine disrupting properties of the lubricating oil composition on exposure to mammals is provided.

In accordance with a sixth embodiment of the present invention, the use of an overbased salt of an oligomerized alkylphenol, wherein the alkyl group of the alkylhydroxyaromatic compound is derived from an olefin mixture comprising propylene pentamers having an initial boiling point of at least about 195° C. and a final boiling point of no more than about 325° C. as measured by ASTM D86, as an additive in a lubricating oil composition comprising a major amount of an oil of lubricating viscosity for the purpose of reducing the endocrine disrupting properties of the lubricating oil composition on exposure to mammals is provided.

The overbased salt of the oligomerized alkylhydroxyaromatic compound of the present invention was determined to be substantially free of endocrine disruptive chemicals when the effects were quantified in an intact juvenile female rat. Accordingly, the overbased salt of the oligomerized alkylhydroxyaromatic compound of the present invention can advantageously be employed in compositions which require endocrine disruption effects when exposed to mammals.

DETAILED DESCRIPTION OF THE PREFERRED EMBODIMENTS

The present invention is directed to an overbased salt of an oligomerized alkylhydroxyaromatic compound wherein the alkyl group of the alkylhydroxyaromatic compound is derived from an olefin mixture comprising propylene oligomers having an initial boiling point of at least about 195° C. and a final boiling point of no more than about 325° C. as measured by ASTM D86.

Prior to discussing the invention in further detail, the following terms will be defined:

DEFINITIONS

As used herein, the following terms have the following meanings, unless expressly stated to the contrary:

The term "endocrine disrupter" as used herein is a compound which disrupts normal regulation of the endocrine system; in particular, the endocrine system that regulates reproductive processes.

The term "lime" as used herein refers to calcium hydroxide, also known as slaked lime or hydrated lime.

The term "Total Base Number" or "TBN" as used herein refers to the amount of base equivalent to milligrams of KOH in 1 gram of sample. Thus, higher TBN numbers reflect more alkaline products, and therefore a greater alkalinity reserve. The TBN of a sample can be determined by ASTM Test No. D2896 or any other equivalent procedure.

The overbased salt of an oligomerized alkylhydroxyaromatic compound of the present invention can be obtained by (a) alkylating a hydroxyaromatic compound with an olefin mixture comprising propylene oligomers having an initial boiling point of at least about 195° C. and a final boiling point of no more than about 325° C. as measured by ASTM D86, to provide an alkylhydroxyaromatic compound; (b) neutralizing the alkylhydroxyaromatic compound of step (a) to provide a salt of the alkylhydroxyaromatic compound; (c) oligomerizing the salt of the alkylhydroxyaromatic compound of step (b) to provide a salt of an oligomerized alkylhydroxyaromatic compound; and (d) overbasing the salt of the oligomerized alkylhydroxyaromatic compound of step (c) to provide the overbased salt of the oligomerized alkylhydroxyaromatic compound.

In general, processes for preparing overbased salts of an oligomerized alkylhydroxyaromatic compound, except for the use of the high initial boiling point propylene oligomers, are well known and any known process for making overbased oligomerized alkylhydroxyaromatic salts may be employed herein. For example, representative processes for preparing such salts include U.S. Pat. Nos. 3,178,368 and 3,801,507 which disclose overbased sulfurized alkylphenates, U.S. Pat. No. 3,429,812 which discloses overbased alkylphenol/formaldehyde/diaminoalkane condensation products, and U.S. Pat. Nos. 5,281,346 and 5,458,793 which disclose neutralized alkylphenol-glyoxylic acid oligomers that may also be overbased. Accordingly, the steps employed in the process for making the overbased salt of an oligomerized alkylhydroxyaromatic compound of the present invention are within the purview of one skilled in the art.

In step (a), a hydroxyaromatic compound is alkylated with an olefin mixture containing at least the propylene oligomers. Useful hydroxyaromatic compounds which may be alkylated include mononuclear monohydroxy and polyhydroxy $C_6$ to $C_{30}$ aromatic hydrocarbons having 1 to 4 hydroxy groups, and preferably 1 to 3 hydroxy groups. Suitable hydroxyaromatic compounds include phenol, catechol, resorcinol, hydroquinone, pyrogallol, cresol, and the like and mixtures thereof. A preferred hydroxyaromatic compound is a phenol.

The olefin mixture for alkylating the hydroxyaromatic compound contains at least propylene oligomers having an initial boiling point of at least about 195° C. and a final boiling point of no more than about 325° C. as measured by ASTM D86. In one embodiment, the propylene oligomers have an initial boiling point of at least about 200° C. as measured by ASTM D86. In another embodiment, the propylene oligomers have an initial boiling point of at least about 210° C. as measured by ASTM D86. In yet another embodiment, the propylene oligomers have an initial boiling point of at least about 220° C. as measured by ASTM D86. In still yet another embodiment, the propylene oligomers have an initial boiling point of at least about 225° C. as measured by ASTM D86. In still another embodiment, the propylene oligomers have an initial boiling point of at least about 230° C. as measured by ASTM D86.

In one embodiment, the propylene oligomers have a final boiling point of no more than about 300° C. as measured by ASTM D86. In another embodiment, the propylene oligomers have a final boiling point of no more than about 290° C. as measured by ASTM D86. In yet another embodiment, the propylene oligomers have a final boiling point of no more than about 280° C. as measured by ASTM D86. Any combination of the foregoing initial boiling points and final boiling points for the propylene oligomers are contemplated herein.

The propylene oligomers are commercially available from such sources as, for example, Chevron Oronite Company LLC and ExxonMobil, or can be prepared by any method known in the art. In a particularly preferred embodiment, a process for preparing the propylene oligomers that can be used in this invention employs a liquid phosphoric acid oligomerization catalyst, see, e.g., the liquid phosphoric acid-catalyzed propylene oligomerization processes disclosed in U.S. Pat. Nos. 2,592,428, 2,814,655 and 3,887,634. The propylene oligomers employed herein typically contain no more than about 20 wt. % and preferably no more than about 15 wt. % of $C_{14}$ or lower carbon number of propylene oligomer, and essentially no significant amount of less than $C_{12}$ propylene oligomer. The propylene oligomers employed herein may contain any amount of low molecular weight propylene oligomer such as propylene trimer or tetramer as long as the initial boiling point of the mixture of propylene oligomers is at least about 195° C.

Generally, the olefin mixture will contain a major mount of the propylene oligomers discussed hereinabove. However, as one skilled in the art will readily appreciate, the olefin mixture can contain other olefins. For example, the other olefins that can be used in the olefin mixture include linear olefins, cyclic olefins, branched olefins other than propylene oligomers such as butylene or isobutylene oligomers, arylalkylenes and the like and mixtures thereof. Suitable linear olefins include 1-hexene, 1-nonene, 1-decene, 1-dodecene and the like and mixtures thereof. Especially suitable linear olefins are high molecular weight normal alpha-olefins such as $C_{16}$ to $C_{30}$ normal alpha-olefins, which can be obtained from processes such as ethylene oligomerization or wax cracking. Suitable cyclic olefins include cyclohexene, cyclopentene, cyclooctene and the like and mixtures thereof. Suitable branched olefins include butylene dimer or trimer or higher molecular weight isobutylene oligomers, and the like and mixtures thereof. Suitable arylalkylenes include styrene, methyl styrene, 3-phenylpropene, 2-phenyl-2-butene and the like and mixtures thereof.

Alkylation of the hydroxyaromatic compound with the olefin mixture is generally carried out in the presence of an alkylation catalyst. Useful alkylation catalysts include Lewis acids, solid acids, trifluoromethanesulfonic acid, and acidic molecular sieve catalysts. Suitable Lewis acids include aluminum trichloride, boron trifluoride and boron trifluoride complexes, such as boron trifluoride etherate, boron trifluoride-phenol and boron trifluoride-phosphoric acid. Suitable solid acids include the sulfonated acidic ion exchange resin type catalysts include Amberlyst 36®, available from Rohm and Hass (Philadelphia, Pa.).

The reaction conditions for the alkylation depend upon the type of catalyst used, and any suitable set of reaction conditions that result in high conversion to the alkylhydroxyaromatic product without unacceptable amounts of cracking can be employed. In a preferred embodiment of the invention, the alkylhydroxyaromatic compound that is the product of alkylation contains no more than about 10%, preferably no more than about 5% of alkylhydroxyaromatic in which the alkyl group is $C_{12}$ or less. Typically, the reaction temperature for the alkylation reaction will be in the range of about 25° C. to about 200° C. and preferably from about 85° C. to about 135° C. The reaction pressure will generally be atmospheric, although higher or lower pressures may be employed. The alkylation process can be practiced in a batchwise, continuous or semi-continuous manner. The molar ratio of the hydroxyaromatic compound to olefin mixture is normally in the range of about 10:1 to about 0.5:1, and preferably will be in the range of about 5:1 to about 3:1.

The alkylation reaction may be carried out neat or in the presence of a solvent which is inert to the reaction of the hydroxyaromatic compound and the olefin mixture. When employed, a typical solvent is hexane.

Upon completion of the reaction, the desired alkylhydroxyaromatic compound can be isolated using conventional techniques. Typically, excess hydroxyaromatic compound is distilled from the reaction product.

The alkyl group of the alkylhydroxyaromatic compound is typically attached to the hydroxyaromatic compound primarily in the ortho and para positions.

The alkylhydroxyaromatic compound thus obtained can then be contacted with a metal base under reactive conditions, preferably in an inert-compatible liquid hydrocarbon diluent to provide a salt of the alkylhydroxyaromatic compound.

Preferably, the reaction is conducted under an inert gas, typically nitrogen. The metal base may be added either in a single addition or in a plurality of additions at intermediate points during the reaction.

Suitable metal basic compounds include hydroxides, oxides or alkoxides of the metal such as (1) an alkali or alkaline earth metal salt derived from a metal base selected from an alkali hydroxide, alkali oxide or an alkali alkoxide, or (2) an alkaline earth metal salt derived from a metal base selected from an alkaline earth hydroxide, alkaline earth oxide or alkaline earth alkoxide. Representative examples of metal basic compounds with hydroxide functionality include lithium hydroxide, potassium hydroxide, sodium hydroxide, magnesium hydroxide, calcium hydroxide, barium hydroxide and aluminum hydroxide. Representative examples of metal basic compounds with oxide functionality include lithium oxide, magnesium oxide, calcium oxide and barium oxide. Preferably, the metal base used is calcium hydroxide because of its handling convenience and cost versus, for example, calcium oxide.

The neutralization reaction between the metal base and the alkylhydroxyaromatic compound is typically conducted at temperatures above room temperature (25° C.). The neutralization reaction is carried out in the presence of a promoter such as ethylene glycol, formic acid, acetic acid, and the like and mixtures thereof.

The salt of the alkylhydroxyaromatic compound is then oligomerized to provide a salt of an oligomerized alkylhydroxyaromatic compound. In theory, neutralization can be conducted as a separate step prior to oligomerization, but neutralization and oligomerization can be carried out together in a single process step. Where the neutralization is conducted as a separate step, both the neutralization and the subsequent oligomerization step are conducted under the same conditions as set forth above.

In one embodiment, oligomerization can be carried out by contacting the salt of the alkylhydroxyaromatic compound with a sulfur source optionally in the presence of an oligomerization promoter. Any suitable sulfur source can be used for the oligomerization step such as, for example, elemental sulfur, hydrogen sulfide, sulfur dioxide and sodium sulfide hydrates. The sulfur can be employed either as molten sulfur or as a solid (e.g., powder or particulate) or as a solid suspension in a compatible hydrocarbon liquid. A suitable oligomerization promoter is a polyol, typically an alkylene diol, e.g., ethylene glycol. Based on one mole of the salt of the alkylhydroxyaromatic compound, typically about 0.5 to about 4, and preferably from about 2 to about 3 moles of sulfur are used.

In conjunction with the promoter or mixture of promoters above, a high molecular weight alkanol can be employed as a co-solvent. These high molecular weight alkanols have straight or branched chain alkyls containing 8 to about 16 carbon atoms, and preferably 9 to about 15 carbon atoms. Representative examples of suitable alkanols include 1-octanol, 1-decanol (decyl alcohol), 2-ethyl-hexanol, and the like. Particularly preferred is 2-ethyl-hexanol. It is beneficial to use a high molecular weight alkanol in the process because it acts as a solvent and also forms an azeotrope with water and hence affords a convenient way to remove the water generated by the neutralization or any other water in the system, by azeotropic distillation either after or preferably during the reaction. The high molecular weight alkanol may also play some part in the chemical reaction mechanism in the sense that it facilitates the removal of the byproduct water during the reaction, thus pushing the reaction to the right of the reaction equation.

In another embodiment, oligomerization can be carried out by contacting the salt of the alkylhydroxyaromatic compound with an aldehyde to form, e.g., a salt of a methylene-bridged alkylhydroxyaromatic compound. Suitable aldehydes include aliphatic aldehydes, aromatic aldehydes, heterocyclic aldehydes and the like and mixtures thereof. Representative examples of such aldehydes include formaldehyde, glyoxylic acid, acetaldehyde, propionaldehyde, butyraldehyde, glycoxal, furaldehyde 2-methyl-propionaldehyde, 2-methyl-butyraldehyde, 3-methyl-butyraldehyde, 2,3-dimethyl-butyraldehyde, 3,3-dimethyl-butyraldehyde, pentanal, methyl substituted pentanal, benzaldehyde, furfural and the like and mixtures thereof. The aldehyde may contain a substituent group such as a hydroxyl, halogen, nitrogen and the like so long as the substituent does not take a major part in the reaction. Preferably, the aldehyde is glyoxylic acid or a formaldehyde component. Formaldehyde is available in many forms for example as a solid, liquid or gas. Particularly preferred is paraformaldehyde (which is a solid typically a powder or flaked product containing the equivalent of about 91% to about 93% formaldehyde). Trioxane a crystalline solid may be employed (trioxane is the cyclic trimer of formaldehyde). However, liquid formaldehyde solutions may also be employed such as formalin solutions (aqueous solutions of formaldehyde, sometimes in methanol, in 37%, 44%, or 50% formaldehyde concentrations are commonly used forms) or formaldehyde in an aqueous solution. Additionally, formaldehyde is also available as a gas.

In another embodiment, oligomerization can be carried out by contacting the salt of the alkylhydroxyaromatic compound with an aldehyde and an amine source in a well-known Mannich reaction. Suitable aldehydes include any of the aldehydes discussed hereinabove. In one embodiment, the amine source contemplated herein is an amine which contains an amino group characterized by the presence of at least one active hydrogen atom. Such amines may contain only primary amino groups, only secondary amino groups, or both primary and secondary groups. The amine may be a mono or polyamine. Representative examples of useful amine compounds include N-methylamine, N-ethylamine, N-n-propylamine, N-isopropylamine, N-n-butylamine, N-isobutylamine, N-sec-butylamine, N-tert-butylamine, N-n-pentylamine, N-cyclopentylamine, N-n-hexylamine, N-cyclohexylamine, N-octylamine, N-decylamine, N-dodecylamine, N-octadecylamine, N-benzylamine, N-(2-phenylethyl) amine, 2-aminoethanol, 3-amino-1-proponal, 2-(2-aminoethoxy)ethanol, N-(2-methoxyethyl)amine, N-(2-ethoxyethyl)amine, N,N-dimethylamine, N,N-diethylamine, N,N-di-n-propylamine, N,N-diisopropylamine, N,N-di-n-butylamine, N,N-di-sec-butylamine, N,N-di-n-pentylamine, N,N-di-n-hexylamine, N,N-dicyclohexylamine, N,N-dioctylamine, N-ethyl-N-methylamine, N-methyl-N-n-propylamine, N-n-butyl-N-methylamine, N-methyl-N-octylamine, N-ethyl-N-isopropylamine, N-ethyl-N-octylamine, N,N-di (2-hydroxyethyl)amine, N,N-di(3-hydroxypropyl)amine, N,N-di(ethoxyethyl)amine, N,N-di(propoxyethyl)amine, ethylene diamine, diethylene triamine, triethylene tetraamine, tetraethylene pentamine, and pentaethylene hexamine, o-, m- and p-phenylene diamine, diamino naphthalenes, N-acetyl tetraethylenepentamine, and the corresponding formyl-, propionyl-, butyryl-, and the like N-substituted compounds, morpholine, thiomorpholine, pyrrole, pyrroline, pyrrolidine, indole, pyrazole, pyrazoline, pyrazolidine, imidazole, imidazoline, imidazolidine, piperidine, phenoxazine, phenthiazine and their substituted analogs, and the like.

In a second embodiment, the amine source is an amino acid or salt thereof. By "amino acid" is meant any organic acid containing at least one primary, secondary or tertiary amine (—N<) group and at least one acidic carboxyl (—COOH) group. Mixtures of different amino acids can be used. Representative examples of amino acids include glycine, alanine, beta-alanine, valine, leucine, isoleucine, phenylalanine, serine, threonine, tyrosine, methionine, 6-aminohexanoic acid, proline, hydroxyproline, tryptophan, histidine, lysine, hydroxylysine, arginine, aspartic acid, asparagine, glutamic acid, glutamine, cysteine, cystine, ethylenediaminetetraacetic acid and nitrilotriacetic acid and other alpha-amino acids containing 1 to 5 carboxyl groups. Particularly preferred are the amino acids which are readily available in commercial quantities such as glycine, β-alanine, nitrilotriacetic acid, etc.

Typical Mannich reactions are well known in the art, for example, as disclosed in U.S. Pat. Nos. 3,368,972, 3,649,229; 4,157,309 and 5,370,805, the contents of which are incorporated by reference herein.

The resulting salt of an oligomerized alkylhydroxyaromatic compound is then overbased by reaction with an acidic overbasing compound, such as carbon dioxide or boric acid. A particularly preferred overbasing process is carbonation, i.e., a reaction with carbon dioxide. Such carbonation can be conveniently effected by addition of a polyol, typically an alkylene diol, e.g., ethylene glycol, and carbon dioxide to the salt of an oligomerized alkylhydroxyaromatic compound. Conveniently, the reaction is conducted by the simple expedient of bubbling gaseous carbon dioxide through the reaction mixture. Excess diluent and any water formed during the overbasing reaction can be conveniently removed by distillation either during or after the reaction.

Another embodiment of the present invention is directed to a lubricating oil composition containing at least (a) a major amount of an oil of lubricating viscosity; and (b) an overbased salt of an oligomerized alkylhydroxyaromatic compound of this invention which is useful as a lubricating oil additive. The lubricating oil compositions can be prepared by admixing, by conventional techniques, an appropriate amount of the lubricating oil additive of this invention with a base oil of lubricating viscosity. The selection of the particular base oil depends on the contemplated application of the lubricant and the presence of other additives. Generally, the overbased salt of an oligomerized alkylhydroxyaromatic compound of this invention will be present in the lubricating oil compositions in an amount of about 0.01 to about 40 wt. % and preferably from about 0.1 to about 20 wt. %, based on the total weight of the lubricating oil composition.

The oil of lubricating viscosity for use in the lubricating oil compositions of this invention, also referred to as a base oil, is typically present in a major amount, e.g., an amount of greater than 50 wt. %, preferably greater than about 70 wt. %, more preferably from about 80 to about 99.5 wt. % and most preferably from about 85 to about 98 wt. %, based on the total weight of the composition. The expression "base oil" as used herein shall be understood to mean a base stock or blend of base stocks which is a lubricant component that is produced by a single manufacturer to the same specifications (independent of feed source or manufacturer's location); that meets the same manufacturer's specification; and that is identified by a unique formula, product identification number, or both. The base oil for use herein can be any presently known or later-discovered oil of lubricating viscosity used in formulating lubricating oil compositions for any and all such applications, e.g., engine oils, marine cylinder oils, functional fluids such as hydraulic oils, gear oils, transmission fluids, etc. Additionally, the base oils for use herein can optionally contain viscosity index improvers, e.g., polymeric alkylmethacrylates; olefinic copolymers, e.g., an ethylene-propylene copolymer or a styrene-butadiene copolymer; and the like and mixtures thereof.

As one skilled in the art would readily appreciate, the viscosity of the base oil is dependent upon the application. Accordingly, the viscosity of a base oil for use herein will ordinarily range from about 2 to about 2000 centistokes (cSt) at 100° Centigrade (C). Generally, individually the base oils used as engine oils will have a kinematic viscosity range at 100° C. of about 2 cSt to about 30 cSt, preferably about 3 cSt to about 16 cSt, and most preferably about 4 cSt to about 12 cSt and will be selected or blended depending on the desired end use and the additives in the finished oil to give the desired grade of engine oil, e.g., a lubricating oil composition having an SAE Viscosity Grade of 0W, 0W-20, 0W-30, 0W-40, 0W-50, 0W-60, 5W, 5W-20, 5W-30, 5W-40, 5W-50, 5W-60, 10W, 10W-20, 10W-30, 10W-40, 10W-50, 15W, 15W-20, 15W-30 or 15W-40. Oils used as gear oils can have viscosities ranging from about 2 cSt to about 2000 cSt at 100° C.

Base stocks may be manufactured using a variety of different processes including, but not limited to, distillation, solvent refining, hydrogen processing, oligomerization, esterification, and rerefining. Rerefined stock shall be substantially free from materials introduced through manufacturing, contamination, or previous use. The base oil of the lubricating oil compositions of this invention may be any natural or synthetic lubricating base oil. Suitable hydrocarbon synthetic oils include, but are not limited to, oils prepared from the polymerization of ethylene or from the polymerization of 1-olefins to provide polymers such as polyalphaolefin or PAO oils, or from hydrocarbon synthesis procedures using carbon monoxide and hydrogen gases such as in a Fischer-Tropsch process. For example, a suitable base oil is one that comprises little, if any, heavy fraction; e.g., little, if any, lube oil fraction of viscosity 20 cSt or higher at 100° C.

The base oil may be derived from natural lubricating oils, synthetic lubricating oils or mixtures thereof. Suitable base oil includes base stocks obtained by isomerization of synthetic wax and slack wax, as well as hydrocracked base stocks produced by hydrocracking (rather than solvent extracting) the aromatic and polar components of the crude. Suitable base oils include those in all API categories I, II, III, IV and V as defined in API Publication 1509, 14th Edition, Addendum I, December 1998. Group IV base oils are polyalphaolefins (PAO). Group V base oils include all other base oils not included in Group I, II, III, or IV. Although Group II, III and IV base oils are preferred for use in this invention, these base oils may be prepared by combining one or more of Group I, II, III, IV and V base stocks or base oils. Useful natural oils include mineral lubricating oils such as, for example, liquid petroleum oils, solvent-treated or acid-treated mineral lubricating oils of the paraffinic, naphthenic or mixed paraffinic-naphthenic types, oils derived from coal or shale, animal oils, vegetable oils (e.g., rapeseed oils, castor oils and lard oil), and the like.

Useful synthetic lubricating oils include, but are not limited to, hydrocarbon oils and halo-substituted hydrocarbon oils such as polymerized and interpolymerized olefins, e.g., polybutylenes, polypropylenes, propylene-isobutylene copolymers, chlorinated polybutylenes, poly(1-hexenes), poly(1-octenes), poly(1-decenes), and the like and mixtures thereof; alkylbenzenes such as dodecylbenzenes, tetradecylbenzenes, dinonylbenzenes, di(2-ethylhexyl)-benzenes, and the like; polyphenyls such as biphenyls, terphenyls, alkylated polyphenyls, and the like; alkylated diphenyl ethers and alkylated diphenyl sulfides and the derivative, analogs and homologs thereof and the like.

Other useful synthetic lubricating oils include, but are not limited to, oils made by polymerizing olefins of less than 5 carbon atoms such as ethylene, propylene, butylenes, isobutene, pentene, and mixtures thereof. Methods of preparing such polymer oils are well known to those skilled in the art.

Additional useful synthetic hydrocarbon oils include liquid polymers of alpha olefins having the proper viscosity. Especially useful synthetic hydrocarbon oils are the hydrogenated liquid oligomers of $C_6$ to $C_{12}$ alpha olefins such as, for example, 1-decene trimer.

Another class of useful synthetic lubricating oils include, but are not limited to, alkylene oxide polymers, i.e., homopolymers, interpolymers, and derivatives thereof where the terminal hydroxyl groups have been modified by, for example, esterification or etherification. These oils are exemplified by the oils prepared through polymerization of ethylene oxide or propylene oxide, the alkyl and phenyl ethers of these polyoxyalkylene polymers (e.g., methyl poly propylene glycol ether having an average molecular weight of 1,000, diphenyl ether of polyethylene glycol having a molecular weight of 500-1000, diethyl ether of polypropylene glycol having a molecular weight of 1,000-1,500, etc.) or mono- and polycarboxylic esters thereof such as, for example, the acetic esters, mixed $C_3$-$C_8$ fatty acid esters, or the $C_{13}$ oxo acid diester of tetraethylene glycol.

Yet another class of useful synthetic lubricating oils include, but are not limited to, the esters of dicarboxylic acids e.g., phthalic acid, succinic acid, alkyl succinic acids, alkenyl succinic acids, maleic acid, azelaic acid, suberic acid, sebacic acid, fumaric acid, adipic acid, linoleic acid dimer, malonic acids, alkyl malonic acids, alkenyl malonic acids, etc., with a variety of alcohols, e.g., butyl alcohol, hexyl alcohol, dodecyl alcohol, 2-ethylhexyl alcohol, ethylene glycol, diethylene glycol monoether, propylene glycol, etc. Specific examples of these esters include dibutyl adipate, di(2-ethylhexyl)sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, the complex ester formed by reacting one mole of sebacic acid with two moles of tetraethylene glycol and two moles of 2-ethylhexanoic acid and the like.

Esters useful as synthetic oils also include, but are not limited to, those made from carboxylic acids having from about 5 to about 12 carbon atoms with alcohols, e.g., methanol, ethanol, etc., polyols and polyol ethers such as neopentyl glycol, trimethylol propane, pentaerythritol, dipentaerythritol, tripentaerythritol, and the like.

Silicon-based oils such as, for example, polyalkyl-, polyaryl-, polyalkoxy- or polyaryloxy-siloxane oils and silicate oils, comprise another useful class of synthetic lubricating oils. Specific examples of these include, but are not limited to, tetraethyl silicate, tetra-isopropyl silicate, tetra-(2-ethylhexyl) silicate, tetra-(4-methyl-hexyl)silicate, tetra-(p-tert-butylphenyl)silicate, hexyl-(4-methyl-2-pentoxy)disiloxane, poly(methyl)siloxanes, poly(methylphenyl)siloxanes, and the like. Still yet other useful synthetic lubricating oils include, but are not limited to, liquid esters of phosphorous containing acids, e.g., tricresyl phosphate, trioctyl phosphate, diethyl ester of decane phosphionic acid, etc., polymeric tetrahydrofurans and the like.

The lubricating oil may be derived from unrefined, refined and rerefined oils, either natural, synthetic or mixtures of two or more of any of these of the type disclosed hereinabove. Unrefined oils are those obtained directly from a natural or synthetic source (e.g., coal, shale, or tar sands bitumen) without further purification or treatment. Examples of unrefined oils include, but are not limited to, a shale oil obtained directly from retorting operations, a petroleum oil obtained directly from distillation or an ester oil obtained directly from an esterification process, each of which is then used without further treatment. Refined oils are similar to the unrefined oils except they have been further treated in one or more purification steps to improve one or more properties. These purification techniques are known to those of skill in the art and include, for example, solvent extractions, secondary distillation, acid or base extraction, filtration, percolation, hydrotreating, dewaxing, etc. Rerefined oils are obtained by treating used oils in processes similar to those used to obtain refined oils. Such rerefined oils are also known as reclaimed or reprocessed oils and often are additionally processed by techniques directed to removal of spent additives and oil breakdown products.

Lubricating oil base stocks derived from the hydroisomerization of wax may also be used, either alone or in combination with the aforesaid natural and/or synthetic base stocks. Such wax isomerate oil is produced by the hydroisomerization of natural or synthetic waxes or mixtures thereof over a hydroisomerization catalyst.

Natural waxes are typically the slack waxes recovered by the solvent dewaxing of mineral oils; synthetic waxes are typically the wax produced by the Fischer-Tropsch process.

The lubricating oil compositions of the present invention may also contain other conventional additives for imparting auxiliary functions to give a finished lubricating oil composition in which these additives are dispersed or dissolved. For example, the lubricating oil compositions can be blended with antioxidants, anti-wear agents, detergents such as metal detergents, rust inhibitors, dehazing agents, demulsifying agents, metal deactivating agents, friction modifiers, pour point depressants, antifoaming agents, co-solvents, package compatibilisers, corrosion-inhibitors, ashless dispersants, dyes, extreme pressure agents and the like and mixtures thereof. A variety of the additives are known and commercially available. These additives, or their analogous compounds, can be employed for the preparation of the lubricating oil compositions of the invention by the usual blending procedures.

Examples of antioxidants include, but are not limited to, aminic types, e.g., diphenylamine, phenyl-alpha-napthylamine, N,N-di(alkylphenyl) amines; and alkylated phenylene-diamines; phenolics such as, for example, BHT, sterically hindered alkyl phenols such as 2,6-di-tert-butylphenol, 2,6-di-tert-butyl-p-cresol and 2,6-di-tert-butyl-4-(2-octyl-3-propanoic) phenol; and mixtures thereof.

Examples of ashless dispersants include, but are not limited to, polyalkylene succinic anhydrides; non-nitrogen containing derivatives of a polyalkylene succinic anhydride; a basic nitrogen compound selected from the group consisting of succinimides, carboxylic acid amides, hydrocarbyl monoamines, hydrocarbyl polyamines, Mannich bases, phosphonoamides, and phosphoramides; triazoles, e.g., alkyltriazoles and benzotriazoles; copolymers which contain a carboxylate ester with one or more additional polar function, including amine, amide, imine, imide, hydroxyl, carboxyl, and the like, e.g., products prepared by copolymerization of long chain alkyl acrylates or methacrylates with monomers of the above function; and the like and mixtures thereof. The derivatives of these dispersants, e.g., borated dispersants such as borated succinimides, may also be used.

Examples of rust inhibitors include, but are not limited to, nonionic polyoxyalkylene agents, e.g., polyoxyethylene lauryl ether, polyoxyethylene higher alcohol ether, polyoxyethylene nonylphenyl ether, polyoxyethylene octylphenyl ether, polyoxyethylene octyl stearyl ether, polyoxyethylene oleyl ether, polyoxyethylene sorbitol monostearate, polyoxyethylene sorbitol monooleate, and polyethylene glycol monooleate; stearic acid and other fatty acids; dicarboxylic acids; metal soaps; fatty acid amine salts; metal salts of heavy sulfonic acid; partial carboxylic acid ester of polyhydric alcohol; phosphoric esters; (short-chain) alkenyl succinic acids; partial esters thereof and nitrogen-containing derivatives thereof; synthetic alkarylsulfonates, e.g., metal dinonylnaphthalene sulfonates; and the like and mixtures thereof.

Examples of friction modifiers include, but are not limited to, alkoxylated fatty amines; borated fatty epoxides; fatty phosphites, fatty epoxides, fatty amines, borated alkoxylated fatty amines, metal salts of fatty acids, fatty acid amides, glycerol esters, borated glycerol esters; and fatty imidazolines as disclosed in U.S. Pat. No. 6,372,696, the contents of which are incorporated by reference herein; friction modifiers obtained from a reaction product of a $C_4$ to $C_{75}$, preferably a $C_6$ to $C_{24}$, and most preferably a $C_6$ to $C_{20}$, fatty acid ester and a nitrogen-containing compound selected from the group consisting of ammonia, and an alkanolamine and the like and mixtures thereof.

Examples of antifoaming agents include, but are not limited to, polymers of alkyl methacrylate; polymers of dimethylsilicone and the like and mixtures thereof.

Each of the foregoing additives, when used, is used at a functionally effective amount to impart the desired properties to the lubricant. Thus, for example, if an additive is a friction modifier, a functionally effective amount of this friction modifier would be an amount sufficient to impart the desired friction modifying characteristics to the lubricant. Generally, the concentration of each of these additives, when used, ranges from about 0.001% to about 20% by weight, and in one embodiment about 0.01% to about 10% by weight based on the total weight of the lubricating oil composition.

The final application of the lubricating oil compositions of this invention may be, for example, in marine cylinder lubricants in crosshead diesel engines, trunk piston engine oils, crankcase lubricants in automobiles and railroads and the like, functional fluids, lubricants for heavy machinery such as steel mills and the like, or as greases for bearings and the like. Whether the lubricating oil composition is fluid or solid will ordinarily depend on whether a thickening agent is present. Typical thickening agents include polyurea acetates, lithium stearate and the like.

In another embodiment of the invention, the lubricating oil additive of the present invention may be provided as an additive package or concentrate in which the additive is incorporated into a substantially inert, normally liquid organic diluent such as, for example, mineral oil, naphtha, benzene, toluene or xylene to form an additive concentrate. These concentrates usually contain from about 20% to about 80% by weight of such diluent. Typically a neutral oil having a viscosity of about 4 to about 8.5 cSt at 100° C. and preferably about 4 to about 6 cSt at 100° C. will be used as the diluent, though synthetic oils, as well as other organic liquids which are compatible with the additives and finished lubricating oil can also be used. The additive package will also typically contain one or more of the various other additives, referred to above, in the desired amounts and ratios to facilitate direct combination with the requisite amount of oil of lubricating viscosity.

The following non-limiting examples are illustrative of the present invention.

EXAMPLE 1

Preparation of Propylene Pentamer Alkylphenol.

To a 30 gallon stainless steel reactor was charged 40.66 kg (432.5 moles) of melted (approximately 45° C.) phenol followed by 30.28 kg (144.2 moles) of propylene pentamer oligomer commercially available from Chevron Oronite Company LLC under a positive nitrogen atmosphere. Next, 3.55 kg of Amberlyst 36® sulfonic acid ion exchange resin was added to the reactor, the mechanical agitator was turned on to 375 rpm, and the reactor pressure was set at 15.18 psia with a vapor vent line temperature of 70° C. (hot water). The reactor was heated to approximately 101° C. over 1 hour and 50 minutes and then held at this temperature for 8 hours. The agitation was then stopped and the reactor was allowed to cool to 79° C. over 15 hours and 35 minutes, and catalyst removed. The reactor contents were distilled to remove unreacted phenol, and then allowed to cool to room temperature. The final distilled product was drained from the bottom of the reactor. The properties of the final product were as follows: Viscosity=1249 cST (40° C.), Hydroxyl Number=167 mg KOH/g of sample, and Bromine Number=38.0 gm $Br_2$/100 g of sample.

EXAMPLE 2

Preparation of Overbased Sulfurized Phenate from Propylene Pentamer Alkylphenol.

To a 3 liter glass reactor fitted with a mechanical stirrer, distillation head vented through a gas scrubber containing 10 wt. % aqueous NaOH solution and a gas inlet tube was added 718.8 g of the product of Example 1, 450.0 g of Exxon 100 N oil, 461.3 g of decyl alcohol, and 72.0 g of Amoco 9221 (an LOB sulfonate). The mixture was agitated and heated to 71° C., and at this temperature 337.5 g lime was added, followed by 112.5 g solid sulfur. The temperature of the reactor was increased to 127° C., at which temperature addition of 116.4 g of ethylene glycol was performed over 45 minutes. After the addition, the reactor temperature was increased to 149° C., and 158.4 g of ethylene glycol was added to the mixture over 25 minutes. After the glycol addition was complete, the temperature was increased to 177° C. over 25 minutes. At this temperature, addition of 120 g of $CO_2$ was begun at an addition rate of 0.564 g/minute. 110 minutes after the $CO_2$ addition was started, 74.4 g of ethylene glycol was added over 15 minutes. After the $CO_2$ addition was complete (210 minutes after it was begun), the reactor was heated to approximately 212° C. under vacuum to distill the alcohol solvent to afford a crude product with a 0.7 Vol % crude sediment. Filtration of this crude product afforded a final product with the following properties: TBN=289, wt. % S=3.58, wt. % Ca=10.7, wt. % $CO_2$=6.65. The viscosity of the final product diluted with Exxon 100 N oil to achieve a 250 TBN was 175 cSt (100° C.).

EXAMPLE 3

Preparation of Overbased Sulfurized Phenate from Propylene Pentamer Alkylphenol.

An overbased sulfurized phenate was prepared in substantially the same manner as in Example 2 to provide a 319 TBN overbased sulfurized Ca phenate concentrate with the following components:
- 467.2 g of the product of Example 1;
- 373.4 g Exxon 100 Neutral Oil;
- 477.2 g decyl alcohol;
- 59.8 g Amoco 9221;
- 280.7 g lime;
- 93.5 g solid sulfur;
- First Ethylene Glycol Charge=131.7 g;
- Second Ethylene Glycol Charge=62.0 g; and
- $CO_2$ Charge=96.0 g at 0.47 g/minute.

The crude product contained a crude sediment of 0.8 Vol % and the filtered crude product had the following properties: TBN=319, wt. % S=3.64, wt. % Ca=11.8, wt. % $CO_2$=7.37.

The viscosity of final product diluted with Exxon 100 N Oil to achieve a 300 TBN was 574.2 cSt (100° C.)

EXAMPLE 4

Preparation of Propylene Pentamer Alkylphenol.

An alkylphenol was made by alkylating a phenol with a propylene pentamer commercially available from Chevron Oronite Company LLC. The propylene pentamer was obtained as the bottoms product of the distillation of propylene oligomer derived from an oligomerization process that employed a bulk liquid phosphoric acid catalyst. The propylene pentamer had an initial boiling point of 236.5° C. and a final boiling point of 295.2° C. and the following carbon number distribution as set forth below in Table 1.

TABLE 1

| | Wt. % |
|---|---|
| C13 | 0.19 |
| C14 | 13.57 |
| C15 | 67.39 |
| C16 | 6.61 |
| C17 | 4.61 |
| C18+ | 7.64 |

Into a 4 liter round flask was added 632.4 g (3 moles) of propylene pentamer (sample 51187) and 1128 g of phenol (12 moles). The reactants were mixed and heated to 90° C. At this temperature, 75.9 g of Amberlyst® 36 catalyst (Rohm and Hass) was added and the temperature of the reaction mixture was raised to 110° C. The reaction proceeded for 4 hours at this temperature under nitrogen at atmospheric pressure. The reaction mixture was cooled to 100° C. and filtered to remove the catalyst. Next, the reaction mixture was heated to 230° C. under 30 mm Hg vacuum and held under those conditions for 10 minutes in order to distill excess phenol. The alkylation was essentially quantitative with respect to phenol, and was greater than 95% monoalkyl and greater than 85% para-directed.

EXAMPLE 5

An alkylphenol was prepared in substantially the same manner as in Example 4 using the same components and amounts.

EXAMPLE 6

Preparation of Propylene Pentamer Alkylphenol.

An alkylphenol was made by alkylating a phenol with a propylene pentamer commercially available from Chevron Oronite Company LLC. The propylene pentamer was obtained as the bottoms product of the distillation of propylene oligomer derived from an oligomerization process that employed a bulk liquid phosphoric acid catalyst. The propylene pentamer had the following carbon number distributions and boiling points as set forth below in Tables 2 and 3, respectively.

TABLE 2

| | Wt. % |
|---|---|
| C12− | 2.09 |
| C13 | 1.22 |
| C14 | 8.77 |
| C15 | 77.07 |

TABLE 2-continued

| | Wt. % |
|---|---|
| C16 | 4.69 |
| C17 | 0.43 |
| C18+ | 5.74 |

TABLE 3

| ASTM D86 Distillation | ° C. |
|---|---|
| Initial Boiling Point (BP) | 230.6 |
| 5% BP | 234.7 |
| 10% BP | 235.4 |
| 50% BP | 240.0 |
| 90% BP | 255.9 |
| 95% BP | 265.4 |
| End Boiling Point | 281.9 |

Into a 4 liter round flask was added 632.4 g (3 moles) of propylene pentamer (sample 51187) and 1128 g of phenol (12 moles). The reactants were mixed and heated to 90° C. At this temperature, 75.9 g of Amberlyst® 36 catalyst (Rohm and Hass) was added and the temperature of the reaction mixture was raised to 110° C. The reaction proceeded for 4 hours at this temperature under nitrogen at atmospheric pressure. The reaction mixture was cooled to 100° C. and filtered to remove the catalyst. Next, the reaction mixture was heated to 230° C. under 30 mm Hg vacuum and held under those conditions for 10 minutes in order to distill excess phenol. The alkylation was essentially quantitative with respect to phenol, and was greater than 95% monoalkyl and greater than 85% para-directed.

EXAMPLE 7

An alkylphenol was prepared in substantially the same manner as in Example 6 using the same components and amounts.

EXAMPLE 8

The alkylphenols of Example 4-7 were blended together in a 1:1:1:1 weight ratio to form an alkylphenol mixture. The alkylphenol mixture was sulfurized and overbased as follows. Into a 4 liter round flask, 800 g of the alkylphenol mixture was mixed with 670.7 g of diluent oil, an oil soluble alkylarylsulfonic acid catalyst and a few drops of an antifoam agent. The mixture was heated to a temperature of 110° C. over a period of 30 minutes. During this period, 380 g of lime was added when the temperature of the mixture reached 70° C.

At 110° C., 112.7 g of sulfur was added and the temperature of the mixture was further increased to 150° C. over a period of 20 minutes under a vacuum of 680 mmHg. The vacuum was applied to remove evolved $H_2S$. After the temperature of 150° C. was reached, 153.7 g of ethylene glycol and 328 g of 2-ethylhexanol were slowly added to the reactor. The temperature of the reactor was further increased to 170° C. over a period of one hour and then maintained for 20 minutes. Carbon dioxide was then introduced at 0.3 g/min and after 15 minutes of carbonation, 79.2 g of ethylene glycol was introduced over a period of one hour. After 30 minutes, the carbon dioxide feeding rate was increased to 0.8 g/min. The total carbon dioxide charge was 120 g. The reaction mixture was then heated to 215° C. and the pressure slowly reduced to 20 mm Hg to remove solvent and ethylene glycol. A nitrogen stripping was done at 80 mm Hg over a period of one hour. The product was cooled to 160° C. with diatomeous earth filter aid.

The properties of the oil concentrate of the overbased salt of the oligomerized alkylphenate of this example are set forth below in Table 4.

TABLE 4

| Property | Result |
| --- | --- |
| Ca, wt. % | 9.76 |
| S, wt. % | 3.22 |
| $CO_2$, wt. % | 5.99 |
| Base number, mg KOH/g | 263 |
| Viscosity @ 100° C., $mm^2/s$ | 274 |

COMPARATIVE EXAMPLE A

The propylene tetramer-derived, $CO_2$ overbased, sulfurized Ca alkylphenate oil concentrate was a commercial material with the properties set forth below in Table 5:

TABLE 5

| Property | Result |
| --- | --- |
| Ca, wt. % | 9.89 |
| S, wt. % | 3.52 |
| $CO_2$, wt. % | 5.44 |
| Base number, mg KOH/g | 262 |
| Viscosity @ 100° C., $mm^2/s$ | 353 |

Testing
Reproductive Toxicity Screening Test

The benefits of employing the overbased salts of the oligomerized alkylhydroxyaromatic compounds of the invention are illustrated by the results of reproductive toxicity tests performed in accordance with the OECD Test Guideline 421. In these tests, rats were dosed with the product of Example 8 and the product of Comparative Example A.

Four individual groups of 12 rats of each sex in the parental (F0) generation were administered daily oral (gavage) dose levels of 0, 60, 250, 1000 mg/kg/day of the $CO_2$ overbased, Ca oligomerized alkylphenate of Example 8. Another four individual groups of 12 rats of each sex in the parental (F0) generation were administered daily oral (gavage) dose levels of 0, 50, 200, 1000 mg/kg/day of the propylene tetramer-derived, $CO_2$ overbased, sulfurized Ca alkylphenate of Comparative Example A. The dosing volume was 5 ml/kg/day. Control animals received the vehicle only, which was a peanut oil dosing solution prepared weekly, and their test material concentrations, homogeneity and stability verified by chemical analysis. Male and female parental animals were dosed daily during the pre-mating (28 days), mating (up to 15 days), gestation (up to 25 days) and lactation (4 days) periods until necropsy.

F0 animals were paired within their groups on a 1:1 basis for mating. Females were examined daily during mating for presence of a copulatory plug or sperm in the vagina. When evidence of mating was not detected within 10 days, the female was placed for up to 5 days with another male from the same group that had previously mated. At completion of parturition, litters were examined for viability. Data for the fertility index (number of females that became pregnant/number of females mated), the mean litter size (average number of (live+dead births)/litter) and the mean live litter size (average number of live births per litter) was recorded and set forth below in Table 6.

TABLE 6

| Test Material | Dose Level (mg/kg/day) | Fertility Index (%) | Mean Live Litter Size |
| --- | --- | --- | --- |
| Comparative Ex. A | 1000 | 91.7 (11/12) | 7.7 |
| | 200 | 91.7 (11/12) | 11.5 |
| | 50 | 91.7 (11/12) | 12.9 |
| | 0 | 100 (12/12) | 12.8 |
| Example 8 | 1000 | 83.3 (10/12) | 13.4 |
| | 250 | 100 (12/12) | 14.0 |
| | 60 | 100 (12/12) | 13.7 |
| | 0 | 91.7 (11/12) | 13.5 |

As the data show, neither the product of Comparative Example A nor the product of Example 8 had any adverse effects on the fertility index. Significantly, the product of Example 8 did not have an adverse effect on the mean live litter size of the rats treated with 1000 mg/kg/day of the product of Example 8 as compared to the mean live litter size of the rats in the control group. However, the mean live litter size of rats treated with 1000 mg/kg/day of the product of Comparative Example A was statistically significantly less than the mean live litter size of the rats in the control group. Moreover, the mean live litter size of the rats treated with 200 mg/kg/day of the product of Comparative Example A was directionally less than the mean live litter size of the rats in the control group. This illustrates the beneficial properties of the overbased salts of the oligomerized alkylhydroxyaromatic compounds of the invention.

Marine Cylinder Lubricant Performance Testing

The efficacy of the overbased, oligomerized alkylhydroxyaromatic salts of the invention was demonstrated by testing various marine cylinder lubricants formulated from these salts. All of the resulting marine cylinder lubricants prepared in the following Examples 9-14 and Comparative Examples B-D possessed a TBN of between 70.5 to 71.8 mg KOH/g oil, a viscosity @ 100° C. of between 17.83 to 18.79 $mm^2/s$, and a Ca content of 2.5 to 2.7 wt. %.

EXAMPLE 9

A marine cylinder lubricant as described above was prepared by adding 28 wt. % of a $CO_2$ overbased, sulfurized 260 TBN Ca alkylphenate oil concentrate derived from the alkylation of phenol with propylene pentamer available from Chevron Oronite Company LLC to a marine cylinder base oil.

EXAMPLE 10

A marine cylinder lubricant as described above was prepared by adding 23.03 wt. % of a $CO_2$ overbased, sulfurized 300 TBN Ca alkylphenate oil concentrate derived from the alkylation of phenol with propylene pentamer available from Chevron Oronite Company LLC to a marine cylinder base oil.

COMPARATIVE EXAMPLE B

A marine cylinder lubricant as described above was prepared by adding 27.77 wt. % of a $CO_2$ overbased, sulfurized 250 TBN Ca alkylphenate oil concentrate derived from the alkylation of phenol with propylene tetramer to a marine cylinder base oil.

EXAMPLE 11

A marine cylinder lubricant as described above was prepared by adding 14 wt. % of the Ca alkylphenate oil concentrate described in Example 9 and 8.47 wt. % of a 420 TBN Ca sulfonate detergent concentrate (app. 50% actives) to a marine cylinder base oil.

EXAMPLE 12

A marine cylinder lubricant as described above was prepared by adding 11.52 wt. % of the Ca alkylphenate oil concentrate described in Example 10 and 8.47 wt. % of the Ca sulfonate detergent concentrate described in Example 11 to a marine cylinder base oil.

COMPARATIVE EXAMPLE C

A marine cylinder lubricant as described above was prepared by adding 13.88 wt. % of the Ca alkylphenate oil concentrate described in Comparative Example B and 8.47 wt. % of the Ca sulfonate detergent concentrate described in Example 11 to a marine cylinder base oil.

EXAMPLE 13

A marine cylinder lubricant as described above was prepared by adding 14 wt. % of the Ca alkylphenate oil concentrate described in Example 9, 8.47 wt. % of the Ca sulfonate detergent concentrate described in Example 11, and 1 wt. % of a polybutene succinimide oil concentrate (app. 50% actives) to a marine cylinder base oil.

EXAMPLE 14

A marine cylinder lubricant as described above was prepared by adding 11.52 wt. % of the Ca alkylphenate oil concentrate described in Example 10, 8.47 wt. % of the Ca sulfonate detergent concentrate described in Example 11, and 1 wt. % of the polybutene succinimide oil concentrate described in Example 13 to a marine cylinder base oil.

COMPARATIVE EXAMPLE D

A marine cylinder lubricant as described above was prepared by adding 13.88 wt. % of the Ca alkylphenate oil concentrate described in Comparative Example B, 8.47 wt. % of the Ca sulfonate detergent concentrate described in Example 11, and 1 weight percent of the polybutene succinimide oil concentrate described in Example 13 to a marine cylinder base oil.

Description of Performance Testing

Falex 3N Corrosive Wear Test

This procedure is used to evaluate the corrosive wear protective properties of marine cylinder lubricants. A steel pin is rotated between two stationary V-blocks immersed in the oil to be tested under load on the V-blocks at a specified temperature and load program. During the test, diluted sulfuric acid is continuously added to the test oil. Tests are generally replicated. The pin wear is determined by weighing the pin before and after the test; the loss in mg is reported as wear.

Indiana Stirring Oxidation Test (ISOT)

This test is used to evaluate bulk oxidative and thermal stability of lubricating oils for internal combustion engines and alike. Two catalyst plates (copper and steel) and a glass varnish rod are immersed in test oil, and the test oil is heated and aerated by stirring for the duration of the test. At the end of the heating period, the viscosity at 40° C. of the test oil is measured, and the increase of the viscosity of the test oil is expressed as the ratio of the viscosity of the test oil to the viscosity of the fresh test oil.

Komatsu Hot Tube (KHT) Test

A lubricating oil composition is passed through a temperature-controlled glass tube for a period of time by employing a suitable air flow. The glass tube is then cooled and washed, and the color of any lacquer deposition remaining on the inner surface of the glass tube is determined using a color merit rating ranging from 0 to 10 (0=black and 10=clean). In cases in which the glass tubes are completely blocked with deposits, the test result is recorded as "blocked".

MAO 64 Micro Coker

This method is used to evaluate the high temperature deposit/lacquer formation tendency of land and marine lubricants. A quantity of test oil is put into a shallow trough of a sloping aluminum panel. A temperature gradient applied to the aluminum panel with the test oil evenly distributed in the shallow trough. The panel is heated for a period of time, and the temperature at which deposits/lacquer starts to form is determined from the appearance of the panel at the end of the test.

Modified Institute of Petroleum 48 (MIP 48) Test

Two samples of a lubricating oil composition were heated for a period of time. Nitrogen was passed through one of the test samples while air was passed through the other sample. The two samples were then cooled, and the viscosities of the samples were determined. The oxidation-based viscosity increase for each lubricating oil composition was calculated by subtracting the kinematic viscosity at 100° C. for the nitrogen-blown sample from the kinematic viscosity at 100° C. for the air-blown sample, and dividing the subtraction product by the kinematic viscosity at 100° C. for the nitrogen blown sample.

Panel Coker Test

This test is used to evaluate the deposit forming or lacquering tendency of marine engine oils on a hot metal surface, simulating the deposit formation in marine engine cylinders and pistons. The lubricant is splashed against a heated test panel under controlled conditions over a prescribed period of time. After the test, the weight of solid decomposition products accumulated on the test panel is determined and expressed as mg deposits.

Pressurized Differential Scanning Calorimeter (PDSC)

This test is used to evaluate thin film oxidation stability of test oils. Heat flow to and from the test oil in a sample cup exposed to oxygen is compared to a heat flow to and from an empty reference cup exposed to oxygen while both cups are heated using a pre-determined temperature profile. The oxidation reaction results in an exothermic reaction which is shown by increased heat flow. The Oxidation Induction Time (OIT) is the time in minutes at which oxidation of the test oil starts.

The performance testing was demonstrated in three different types of formulations: phenate-only (Table 7), phenate-sulfonate (Table 8), and phenate-sulfonate with dispersant (Table 9). As the data show, the overbased, oligomerized phenates of the invention perform their detergent functions relatively equal to detergents derived from propylene tetramer.

TABLE 7

Phenate-only MCLs

| PERFORMANCE TESTS: | | Ex. 9 | Ex. 10 | Comp. Ex. B |
|---|---|---|---|---|
| Falex 3N Corrosive Wear Test, Pin Weight Loss, mg | | 130/94 | 126/95 | 102/108 |
| ISOT Visc. Increase (40° C.), ratio | | 1.18 | 1.14 | 1.24 |
| Komatsu Hot Tube, 10 = clean | Lacquer @310° C. | 7.00 | 6.50 | 7.00 |
| | Lacquer @320° C. | 6.50 | Blocked | 6.50 |
| MAO 64 Micro Coker, Deposit Formation Temperature, ° C. | | 246/251 | 258/264 | 238/245 |
| MIP-48 Oxidation, % Viscosity Increase | | 45.6 | 40.6 | 59.8 |
| Panel Coker, mg deposits | | 217 | 276 | 284 |
| PDSC OIT, min. | | 134.0 | 107.0 | 142.0 |

TABLE 8

Phenate-sulfonate MCLs

| PERFORMANCE TESTS: | | Ex. 11 | Ex. 12 | Comp. Ex C |
|---|---|---|---|---|
| Falex 3N Corrosive Wear Test, Pin Weight Loss, mg | | 149/108 | 113/132 | 118/130 |
| ISOT Visc. Increase (40° C.), ratio | | 1.09 | 1.07 | 1.09 |
| Komatsu Hot Tube, 10 = clean | Lacquer @310° C. | 7.50 | 7.00 | 7.00 |
| | Lacquer @320° C. | Blocked | Blocked | 6.5 to 7.0 |
| MAO 64 Micro Coker, Deposit Formation Temperature, ° C. | | 260/259 | 253/254 | 261/263 |
| MIP-48 Oxidation, % Viscosity Increase | | 54.3 | 91.3 | 40.7 |
| Panel Coker, mg deposits | | 180 | 226 | 246 |
| PDSC OIT, min. | | 82.0 | 64.6 | 80.0 |

TABLE 9

Phenate-sulfonate-dispersant MCLs

| | | Sample | | |
|---|---|---|---|---|
| PERFORMANCE TESTS: | | Ex. 13 | Ex. 14 | Comp. Ex. D |
| Falex 3N Corrosive Wear Test, Pin Weight Loss, mg | | 5/71/66 | 96/35/34 | 16/29 |
| ISOT Visc. Increase (40° C.), ratio | | 1.06 | 1.05 | 1.07 |
| Komatsu Hot Tube, 10 = clean | Lacquer @310° C. | 8.00 | 7.00 | 7.00 |
| | Lacquer @320° C. | 7.00 | Blocked | 5.50 |
| MAO 64 Micro Coker, Deposit Formation Temperature, ° C. | | 261/262 | 252/259 | 261/260 |
| MIP-48 Oxidation, % Viscosity Increase | | Not measured | 89.2 | 37.2 |
| Panel Coker, mg deposits | | 271 | 242 | 222 |
| PDSC OIT, min. | | 65.0 | 38.0 | 85.8 |

It will be understood that various modifications may be made to the embodiments disclosed herein. Therefore the above description should not be construed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the claims appended hereto.

What is claimed is:

1. An overbased salt of an oligomerized alkylhydroxyaromatic compound, wherein the alkyl group of the alkylhydroxyaromatic compound is derived from an olefin mixture comprising propylene oligomers having an initial boiling point of at least about 195° C. and a final boiling point of no more than about 325° C. as measured by ASTM D86.

2. The overbased salt of claim 1, wherein the propylene oligomers have an initial boiling point of at least about 200° C. as measured by ASTM D86.

3. The overbased salt of claim 1, wherein the propylene oligomers have an initial boiling point of at least about 210° C. as measured by ASTM D86.

4. The overbased salt of claim 1, wherein the propylene oligomers have an initial boiling point of at least about 225° C. as measured by ASTM D86.

5. The overbased salt of claim 1, wherein the propylene oligomers have an initial boiling point of at least about 230° C. as measured by ASTM D86.

6. The overbased salt of claim 1, wherein the propylene oligomers have a final boiling point of no more than about 300° C. as measured by ASTM D86.

7. The overbased salt of claim 1, wherein the propylene oligomers have a final boiling point of no more than about 290° C. as measured by ASTM D86.

8. The overbased salt of claim 1, wherein the propylene oligomers have a final boiling point of no more than about 280° C. as measured by ASTM D86.

9. The overbased salt of claim 1, wherein the propylene oligomers have an initial boiling point of at least about 230° C. and a final boiling point of no more than about 280° C. as measured by ASTM D86.

10. The overbased salt of claim 1, wherein the salt is an alkali or alkaline earth metal salt.

11. The overbased salt of claim 10, wherein the alkali metal salt is derived from a metal base selected from an alkali oxide or alkali hydroxide.

12. The overbased salt of claim 10, wherein the alkaline earth metal salt is derived from a metal base selected from an alkaline earth oxide or alkaline earth hydroxide.

13. The overbased salt of claim 10, wherein the metal base is selected from the group consisting of calcium oxide, calcium hydroxide, magnesium oxide, magnesium hydroxide, and mixtures thereof.

14. The overbased salt of claim 1, wherein the hydroxyaromatic compound is a phenol.

15. The overbased salt of claim 1, wherein the hydroxyaromatic compound is a phenol and the olefin mixture comprises propylene pentamers.

16. The overbased salt of claim 9, wherein the hydroxyaromatic compound is a phenol and the olefin mixture comprises propylene pentamers.

17. The overbased salt of claim 1, wherein the oligomerized alkylhydroxyaromatic compound is a sulfurized alkylhydroxyaromatic compound.

18. A process for preparing an overbased salt of an oligomerized alkylhydroxyaromatic compound, the process comprising the steps of:
(a) alkylating a hydroxyaromatic compound with an olefin mixture comprising propylene oligomers having an initial boiling point of at least about 195° C. and a final boiling point of no more than about 325° C. as measured by ASTM D86, to provide an alkylhydroxyaromatic compound;
(b) neutralizing the alkylhydroxyaromatic compound of step (a) to provide a salt of the alkylhydroxyaromatic compound;
(c) oligomerizing the salt of the alkylhydroxyaromatic compound of step (b) to provide a salt of an oligomerized alkylhydroxyaromatic compound; and
(d) overbasing the salt of the oligomerized alkylhydroxyaromatic compound of step (c) to provide the overbased salt of the oligomerized alkylhydroxyaromatic compound.

19. The process of claim 18, wherein the propylene oligomers have an initial boiling point of at least about 230° C. and a final boiling point of no more than about 280° C. as measured by ASTM D86.

20. The process of claim 18, wherein the step of neutralizing comprises contacting the alkylhydroxyaromatic compound of step (a) with an alkali or alkaline earth metal salt.

21. The process of claim 18, wherein the step of neutralizing comprises contacting the alkylhydroxyaromatic compound of step (a) with a metal base selected from the group consisting of calcium oxide, calcium hydroxide, magnesium oxide, magnesium hydroxide, and mixtures thereof.

22. The process of claim 18, wherein the hydroxyaromatic compound is a phenol.

23. The process of claim 18, wherein the hydroxyaromatic compound is a phenol and the olefin mixture comprises propylene pentamers.

24. The process of claim 19, wherein the hydroxyaromatic compound is a phenol and the olefin mixture comprises propylene pentamers.

25. The process of claim 18, wherein the step of oligomerizing comprises sulfurizing the salt of the alkylhydroxyaromatic compound of step (b).

26. A lubricating oil composition comprising (a) a major amount of an oil of lubricating viscosity; and (b) an overbased salt of an oligomerized alkylhydroxyaromatic compound, wherein the alkyl group of the alkylhydroxyaromatic compound is derived from an olefin mixture comprising propylene oligomers having an initial boiling point of at least about 195° C. and a final boiling point of no more than about 325° C. as measured by ASTM D86.

27. The lubricating oil composition of claim 26, wherein the base oil of lubricating viscosity is comprised of a mineral base oil.

28. The lubricating oil composition of claim 26, wherein the propylene oligomers have an initial boiling point of at least about 200° C. as measured by ASTM D86.

29. The lubricating oil composition of claim 26, wherein the propylene oligomers have an initial boiling point of at least about 210° C. as measured by ASTM D86.

30. The lubricating oil composition of claim 26, wherein the propylene oligomers have an initial boiling point of at least about 225° C. as measured by ASTM D86.

31. The lubricating oil composition of claim 26, wherein the propylene oligomers have an initial boiling point of at least about 230° C. as measured by ASTM D86.

32. The lubricating oil composition of claim 26, wherein the propylene oligomers have a final boiling point of no more than about 300° C. as measured by ASTM D86.

33. The lubricating oil composition of claim 26, wherein the propylene oligomers have a final boiling point of no more than about 290° C. as measured by ASTM D86.

34. The lubricating oil composition of claim 26, wherein the propylene oligomers have a final boiling point of no more than about 280° C. as measured by ASTM D86.

35. The lubricating oil composition of claim 26, wherein the propylene oligomers have an initial boiling point of at least about 230° C. and a final boiling point of no more than about 280° C. as measured by ASTM D86.

36. The lubricating oil composition of claim 26, wherein the overbased salt is derived from a metal base selected from the group consisting of calcium oxide, calcium hydroxide, magnesium oxide, magnesium hydroxide, and mixtures thereof.

37. The lubricating oil composition of claim 26, wherein the hydroxyaromatic compound is a phenol.

38. The lubricating oil composition of claim 26, wherein the hydroxyaromatic compound is a phenol and the olefin mixture comprises propylene pentamers.

39. The lubricating oil composition of claim 26, wherein the oligomerized alkylhydroxyaromatic compound is a sulfurized alkylhydroxyaromatic compound.

40. The lubricating oil composition of claim 26, wherein the overbased salt is present in the lubricating oil composition in an amount of about 0.01 wt. % to about 40 wt. %, based on the total weight of the composition.

41. The lubricating oil composition of claim 26, further comprising at least one additive selected from the group consisting of metallic detergents, ashless dispersants, friction modifiers, extreme pressure agents, viscosity index improvers and pour point depressants.

42. The lubricating oil composition of claim 26, having a phosphorous content not exceeding 0.05 wt. %, based on the total weight of the composition.

43. A method for reducing the endocrine disrupting properties of a lubricating oil composition on exposure to mammals, the method comprising adding the overbased salt of the oligomerized alkylhydroxyaromatic compound of claim 1 to a lubricating oil composition comprising a major amount of an oil of lubricating viscosity.

44. A method for reducing the endocrine disrupting properties of a lubricating oil composition on exposure to mammals, the method comprising adding the overbased salt of the oligomerized alkylhydroxyaromatic compound of claim 16 to a lubricating oil composition comprising a major amount of an oil of lubricating viscosity.

45. A method for reducing the endocrine disrupting properties of a lubricating oil composition on exposure to mammals, the method comprising adding the overbased salt of the oligomerized alkylhydroxyaromatic compound of claim 17 to a lubricating oil composition comprising a major amount of an oil of lubricating viscosity.

* * * * *